United States Patent [19]

Zdrojkowski

[11] 4,122,843
[45] Oct. 31, 1978

[54] ELECTRODE SYSTEM FOR A HEART RATE MONITOR

[75] Inventor: Ronald J. Zdrojkowski, Pittsburgh, Pa.

[73] Assignee: Electro-Technics, Inc., Pittsburgh, Pa.

[21] Appl. No.: 823,283

[22] Filed: Aug. 10, 1977

[51] Int. Cl.² ............................................. A61B 5/04
[52] U.S. Cl. ...................... 128/2.06 E; 128/DIG. 4
[58] Field of Search .......... 128/2.06 E, 2.1 E, DIG. 4

[56] References Cited

U.S. PATENT DOCUMENTS

| | | | |
|---|---|---|---|
| 3,500,823 | 3/1970 | Richardson et al. | 128/2.06 E |
| 3,547,104 | 12/1970 | Buffington | 128/2.06 E |
| 3,606,881 | 9/1971 | Woodson | 128/2.06 E |
| 3,620,208 | 11/1971 | Higley et al. | 128/2.06 E |
| 3,826,246 | 7/1974 | Raddi et al. | 128/2.06 E |
| 3,830,227 | 8/1974 | Green | 128/2.06 E X |
| 3,868,947 | 3/1975 | Holsinger | 128/2.06 E |
| 3,888,240 | 6/1975 | Reinhold, Jr. et al. | 128/2.06 E |
| 4,026,278 | 5/1977 | Ricketts et al. | 128/2.06 E |

FOREIGN PATENT DOCUMENTS 1,164,770  5/1958  France ..................... 128/2.06 E

OTHER PUBLICATIONS

Potter et al., "Capacitive Type ... Electrode", IEEE Trans on Bio-Med Eng., Oct. 1970, pp. 350-351.
Lagow et al., "Anodic Insulated ... Electrodes", IEEE Trans on Bio-Med Eng., Mar. 1971, pp. 162-164.

*Primary Examiner*—Lee S. Cohen
*Attorney, Agent, or Firm*—Brown, Flick & Peckham

[57] ABSTRACT

Two signal electrodes and a reference electrode are attached to dielectric members, from which their front faces project for engaging a person's skin. Embedded in the dielectric members that enclose the two signal electrodes are electrostatic shields that are behind the electrodes and spaced from them. There are electrical conductors for connecting the signal electrodes to the differential amplifier of a heart rate monitor, and other electrical conductors for connecting the shields and the reference electrode to the common input terminal of the amplifier.

8 Claims, 3 Drawing Figures

ELECTRODE SYSTEM FOR A HEART RATE MONITOR

It is not unusual for cardiologists to prescribe exercise programs for their heart patients in order to raise their heart rates to prescribed levels for a standard length of time. This builds cardio-respiratory endurance. If there is to be control of the intensity of exercise there should be heart rate feedback to the patient. This can be accomplished by a heart rate monitor connected to the patient by electrodes. The determination of heart rate generally chosen in clinical and laboratory situations is by the electrocardiogram of the exercising subject. The electrocardiogram is usually obtained from electrodes located on the patient's chest. The most commonly used electrodes in clinical and laboratory practice utilize a conductive metal that is physically separated from the skin and which makes electrical connection with the skin by means of a conductive gel or paste. Such electrodes usually are attached to the skin by means of an adhesive. Furthermore, in order to obtain good low resistance electrical contact to the body, the subject's skin must be carefully cleaned and often is abraded in order to reduce the thickness of the horny layer of skin under the electrode.

While all of the above steps are acceptable for occasional use by a given subject, they are not acceptable for long term daily use because the skin preparation is inconvenient and time consuming, the electrode application requires some skill, and the skin cleaning and the electrode adhesive and/or the conductive gel can cause objectionable skin irritation.

It is among the objects of this invention to provide an electrode system for a heart rate monitor which is simple to apply by an unskilled individual, which is comfortable and does not produce irritation in long term use, which is convenient to use on a daily basis, which requires no special electrode paste or gel, which is inexpensive, which produces reliable ECG pickup during vigorous exercise and which is reusable.

The preferred embodiment of the invention is illustrated in the accompanying drawings, in which FIG. 1 is a fragmentary view of the body-engaging side of a belt carrying the electrodes;

Figure 1:
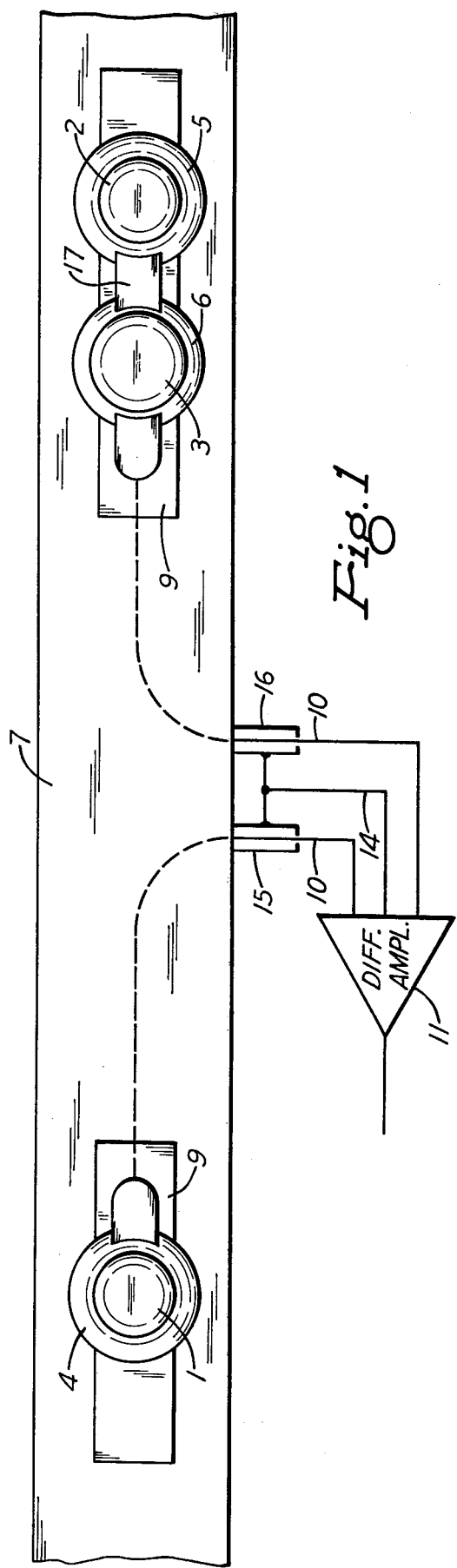

Referring to FIG. 1 of the drawings, there are two signal electrodes 1 and 2 and one reference electrode 3. Preferably, each of these electrodes is formed from a plastic loaded with electrically conductive particles, such as, a mixture of silicone rubber or polyvinyl chloride and carbon particles molded into the general shape of a disc. Each electrode is supported by a dielectric member 4, 5 or 6 that may also be silicone rubber or polyvinyl chloride. The electrodes project a short distance from these members, the backs of which are flat. These electrodes are intended to be held against the chest of a user by an elastic belt 7. For this purpose the flat back of each dielectric member preferably is provided with a Velcro patch 8 (FIGS. 2 and 3), the cooperating member of which is a strip 9 secured to the inner surface of the belt so that the electrodes can be attached to the belt in any desired location and quickly removed. Each of the two signal electrodes is connected by an insulated wire 10 to the differential amplifier 11 in a heart monitor (not shown).

With the signal electrodes as described thus far, static electric discharges in their vicinity could cause electrical interference that could trigger the heart beat detection circuits. Also, displacement currents could be produced in the electrode-to-skin interface simply by moving a conductor in the vicinity of an electrode without actually touching the electrode. With conventional electrodes, the electrode-to-skin impedance is lowered considerably by cleaning and abrading the skin and by using a highly conductive electrode paste as mentioned above. In such cases, the currents produced by the noise sources cause only a small voltage drop across the electrode-to-skin interface and so their interference effect is minimized, but since it is intended that the electrodes described herein shall be used dry with unprepared skin, steps must be taken to minimize noise currents through the electrode-skin interface. This is accomplished, in accordance with this invention, by completely shielding the signal electrodes and the wires connected to them, the shielding being connected to the user's body by means of the reference electrode, which is the common electrode of a differential amplifier input system.

Figure 2:
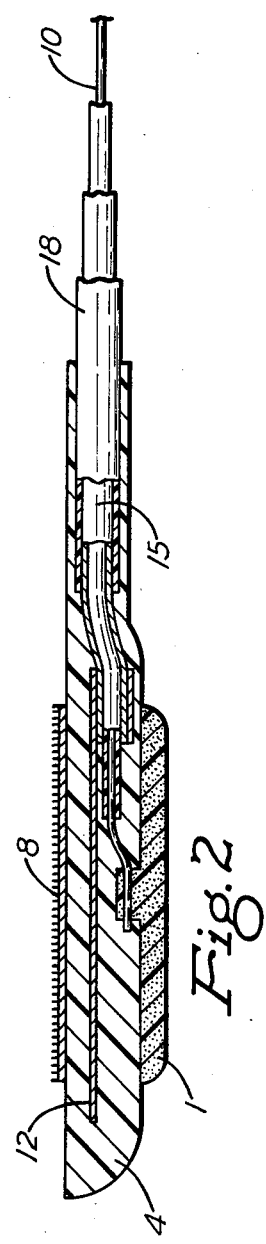
FIG. 2 is an enlarged horizontal section of the left-hand electrode.
Figure 3:
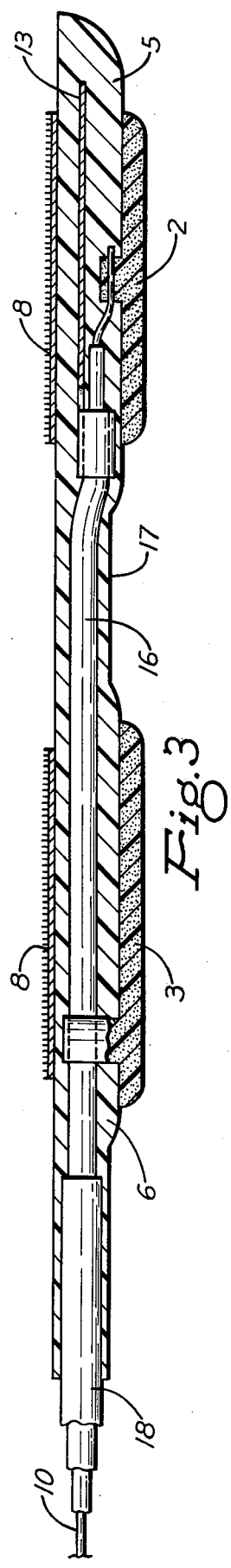
FIG. 3 is an enlarged horizontal section of the remaining electrodes.

Thus, as shown in FIG. 2 of the drawings, an electrostatic shield 12 is embedded in dielectric member 4 and a like shield 13 is embedded in dielectric member 5. the shields can be any suitable conductor, such as metal foil or merely a paint made from the same material as the electrodes. These shields are electrically insulated from electrodes 1 and 2. Shield 12 is electrically connected with the common input line 14 of the amplifier by means of an electrical conductor 15 in the form of a flexible metal sheath enclosing the insulated wire 10 connected to electrode 1, whereby the sheath also shields the wire. The electrode ends of the sheath and wire are embedded in the dielectric member, which holds them in place.

Shield 13 is connected with the common input of the amplifier in the same way, by a flexible metal sheath 16 encircling wire 10 and shielding it. This same shielding sheath is electrically connected to the reference electrode 3. This can be done by molding a short length of the sheath and wire 10 in dielectric member 6 parallel to electrode 3, with an electrical connection between the electrode 3 and sheath. Preferably, dielectric members 5 and 6 are integrally connected by a short length 17 of dielectric material molded around the sheath between the two dielectric members. The shielding sheaths around the conductor wires 10 are enclosed in insulation 18.

The noise currents caused by sources external to the patient's body pass into the shields and then into his body through the common electrode 3. Consequently, the noise potentials produced by the voltage drop across this common electrode-to-skin interface appear as a common mode signal to electrodes 1 and 2 and so can be eliminated by a differential input amplifier. the ECG signal, however, remains as a differential voltage between electrodes 1 and 2 and is not affected by the shielding.

One of the functions of an electrode paste in conventional electrode systems is to provide a flexible coupling between the skin and the rigid electrode. If such a paste is not used, the electrodes must be in direct contact with the skin, but then mechanical disturbance of this interface can cause large and rapid voltage changes that can falsely trigger the heart beat detection circuits. This is not much of a problem as long as the skin is nearly dry because the changes in potential, due to electrical noise generated with mechanical disturbances of the electrodes, vary slowly with time and can easily be distinquished from the rapidly changing components in the ECG waveform. It is these rapidly changing components that are used in detecting the heartbeat. However, in the past, as the level of perspiration increased between the electrodes and the skin, the high frequency content of the noise components caused by mechanical disturbances also increased and was difficult to distinquish from the ECG signal and therefore could lead to false heartbeat detection.

The heavy perspiration problem is solved by two features of this invention. The first is the raised or projecting front face of each electrode, which serves to provide a high pressure between the electrode and the skin, but not so high as to cause discomfort. This high pressure helps to keep heavy perspiration from remaining between electrode and skin. The second feature is that the exposed faces of the electrodes are roughened by an abrasive, such as medium grit sandpaper. This provides improved control of the liquid film of perspiration and greatly reduces the interference effects of heavy perspiration. No perspiration can come in contact with the shielding and metal wires because everything is well protected by insulating material. The electrode system is water tight.

According to the provisions of the patent statutes, I have explained the principle of my invention and have illustrated and described what I now consider to represent its best embodiment. However, I desire to have it understood that, within the scope of the appended claims, the invention may be practiced otherwise than as specifically illustrated and described.

I claim:

1. An electrode system for a heart rate monitor having a differential amplifier, comprising two signal electrodes and a reference electrode each having a front face for engaging a person's skin, a dielectric member supporting each electrode with said front face exposed, means for holding said dielectric members with said electrode faces positioned to engage the skin, electrostatic shields embedded in the dielectric members that support the signal electrodes, the shield being behind the signal electrodes and electrically insulated therefrom, a first pair of electrical conductors connected to the signal electrodes and adapted to electrically connect them with a differential amplifier, a second pair of electrical conductors connected to said shields and adapted to electrically connect them to the common input of the amplifier, and means electrically connecting one of said shields with said reference electrode.

2. An electrode system according to claim 1, in which said second pair of electrical conductors are metal sheaths encircling said first electrical conductors, one of said sheaths being connected to one of said shields, and the other sheath being connected to both the other shield and the reference electrode.

3. An electrode system according to claim 2, in which a molded dielectric bridging member surrounds said other sheath between the dielectric members enclosing said other shield and the reference electrode and is integral with said last-mentioned dielectric members.

4. An electrode system according to claim 3, in which the surfaces of said dielectric members behind said shields are substantially flat, and said sheaths and first conductors extend laterally from said members.

5. An electrode system according to claim 1, in which each of said electrodes is formed from polyvinyl chloride loaded with carbon particles.

6. An electrode system according to claim 1, in which each of said electrodes is formed from silicone rubber loaded with carbon particles.

7. An electrode system according to claim 1, in which said skin engaging face of each of the electrodes is roughened.

8. An electrode system according to claim 1, in which said electrodes project from said dielectric members.

* * * * *